United States Patent
Lanz

(10) Patent No.: US 8,702,706 B2
(45) Date of Patent: Apr. 22, 2014

(54) PELVIC CLAMP

(75) Inventor: Andreas Lanz, Lyss (CH)

(73) Assignee: Depuy Synthes Products, LLC, Raynham, MA (US)

(*) Notice: Subject to any disclaimer, the term of this patent is extended or adjusted under 35 U.S.C. 154(b) by 726 days.

(21) Appl. No.: 11/915,100

(22) PCT Filed: May 23, 2006

(86) PCT No.: PCT/IB2006/051650
§ 371 (c)(1),
(2), (4) Date: Jul. 11, 2008

(87) PCT Pub. No.: WO2006/126167
PCT Pub. Date: Nov. 30, 2006

(65) Prior Publication Data
US 2009/0216231 A1    Aug. 27, 2009

Related U.S. Application Data

(60) Provisional application No. 60/684,475, filed on May 24, 2005.

(51) Int. Cl.
*A61F 5/04* (2006.01)
(52) U.S. Cl.
USPC .............................................. 606/59
(58) Field of Classification Search
USPC ................................ 606/53–59, 90
See application file for complete search history.

(56) References Cited

U.S. PATENT DOCUMENTS

| | | | |
|---|---|---|---|
| 4,292,964 A * | 10/1981 | Ulrich | 606/80 |
| 5,059,194 A * | 10/1991 | Michelson | 606/90 |
| 5,196,012 A * | 3/1993 | Malka | 606/54 |
| 5,300,071 A * | 4/1994 | Browner et al. | 606/57 |
| 6,162,222 A | 12/2000 | Poka et al. | |
| 6,635,072 B1 * | 10/2003 | Ramamurti et al. | 606/208 |
| 6,860,883 B2 | 3/2005 | Janowsli et al. | |
| 2005/0027303 A1 | 2/2005 | Lionberger et al. | |

FOREIGN PATENT DOCUMENTS

| | | |
|---|---|---|
| DE | 2901962 | 7/1980 |
| EP | 1488750 | 12/2004 |

* cited by examiner

Primary Examiner — Jerry Cumberledge
Assistant Examiner — Nicholas Plionis
(74) Attorney, Agent, or Firm — Fay Kaplun & Marcin, LLP

(57) ABSTRACT

A pelvic clamp has a rail-like straight guide for two arms which are displaceable relative to one another along this straight guide and project from the straight guide and on each of the free ends of which an approximately tubular carrier for a tip intended for bone contact is provided. A locking device releasable using at least one handle is provided between the two parts displaceable relative to one another, namely between at least one of the arms and the straight guide. Preferably at least one of the arms preferably both arms, is or are capable of being folded or dismantled and thus shortened via at least one joint which can be fixed in a desired position and/or a plug connection.

18 Claims, 4 Drawing Sheets

PELVIC CLAMP

FIELD OF THE INVENTION

The invention relates to a pelvic clamp having a rail-like straight guide for two arms which are displaceable relative to one another along this straight guide and project from the straight guide and on each of the free ends of which a tip intended for bone contact is provided. Such pelvic clamps are also known as an "emergency pelvic clamp".

BACKGROUND OF THE INVENTION

A pelvic clamp of the type mentioned at the outset is disclosed, for example, in CH-A5-680561, has long been on the market and has proved its worth. For example, the procedure using it is described in the journal "Operative Orthopädie und Traumatologie [Surgical orthopaedics and traumatology]", 2004, no. 2, pages 192-198. Although the present invention is not limited thereto it should be mentioned that a rail having a square profile was used as a rail-like straight guide in the case of the known pelvic clamp frequently referred to in the technical literature as "C-clamp". The square profile ensures good guidance and is fairly torsionally rigid, and it is for this reason that it is also preferred for the present invention. However, it would of course also be possible within the scope of the invention, for example, to fix the position of two round profile rods parallel to one another in a frame.

During the use of the known pelvic clamp, certain problems have arisen which would permit a further improvement. In order to carry out a fixing of the position after driving the tip on the clamp nail in the correct position into the ilium, the two arms are moved relative to one another along the straight guide (i.e. in actual fact, it would also be sufficient to connect one arm firmly to the straight guide and to move only the other arm) whereupon the threaded spindles carrying the tips are screwed against the patient's pelvis until the rail bends. However, this means that canting occurs between rail and arms, which may be extremely disadvantageous on loosening.

SUMMARY OF THE INVENTION

According to a first exemplary aspect of the present invention, between the two parts displaceable relative to one another, namely between at least one of the arms and the straight guide, a locking device is detachable by means of at least one handle. As a result, the forces on adjustment of the spacing of the two arms from one another act mainly in the region of the straight guide.

These smaller forces—now not transmitted by the lever action of the arms—lead to no canting or bending at the straight guide. In addition, the adjustment can be carried out in a simple manner according to the invention by displacing the arms along the straight guide, it then being possible to lock the arms easily in their respective position. This carrier (hollow nail) holding the tip, preferably in the form of a Kirschner wire inserted through its hollow interior, can then—as corresponds to a preferred embodiment of the invention—be fixed by means of a fixing arrangement on its arm so as to be non displaceable in the longitudinal direction. However, the invention also covers variants in which compression by means of threaded spindles known per se is possible in addition to the fast displacement and fast locking.

According to a second exemplary aspect of the present invention, at least one of the arms, preferably both arms, is or are capable of being folded and thus shortened by means of at least one joint which can be fixed in a desired position and/or a plug connection. The pelvic clamp can thus be housed in conventional containers for transport and/or for sterilization. Of course, this solution is inventive per se independently of the question as to whether or not a locking device which can be released by a handle is now present. Thus, it is actually a separate inventive idea, although the combination of the two concepts leads to particularly improved handling properties. The fixing of the joint can be effected in various ways, for example by means of a friction clutch which can be tightened.

However, since continuous adjustment would in any case not be required, it is more advantageous if the joint has a joint arc, and an indentation for fixing the position is provided either on the arc or on an arm section opposite it, preferably on the joint arc, into which indentation a projection, in particular on the respective other part, for example a bolt, can be inserted. In other words a preferred novel pelvic clamp can be fixed in a position of use and in a transport position.

The pelvic clamp according to the invention can be produced so as to have very low weight if at least one part thereof consists of light metal, such as aluminium or an aluminium alloy. The light metal can be processed, for example, in the pasty, semi solid state because such alloys have relatively low brittleness. Instead of aluminium (if need be duraluminium) magnesium or one of its alloys may also be used.

BRIEF DESCRIPTION OF THE DRAWINGS

Further details of the invention are evident from the following description of working examples shown schematically in the drawing. The figures are described as a whole, and identical reference numerals denote identical components.

DETAILED DESCRIPTION OF THE DRAWINGS

Figure 1A:
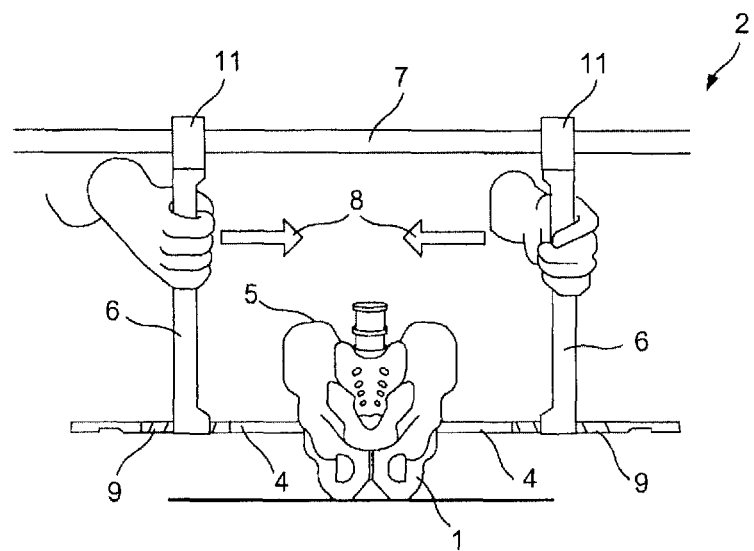
FIGS. 1*a* and 1*b* show the mounting of a pelvic clamp on a patient with an unstable pelvic fracture, FIG. 1*a* illustrating the clamp in a section through the patient's body, and FIG. 1*b* illustrating the application of the nails for exact positioning of the clamp.
Figure 1B:
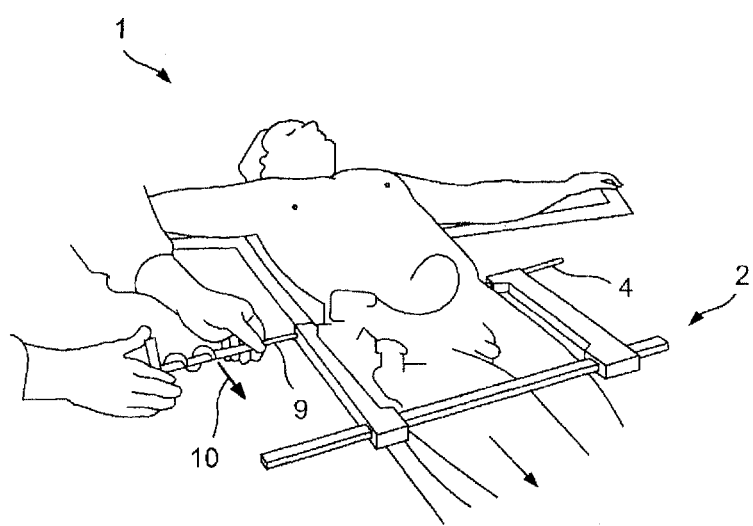

FIGS. 1*a* and 1*b* show how a pelvic clamp 2 is positioned on a patient 1 with an unstable pelvic fracture. For this purpose a clamp nail 4 is passed through the body of the anaesthetised patient 1 at a certain point of the ilium 5.

The clamp nails 4 are held at the free ends by arms 6, which arms 6 can be displaced along a rail-like straight guide 7 (in the direction of the arrows 8 in FIG. 1*a*), in order to adapt the C-shaped pelvic clamp 2 to the dimensions of the patient 1 and to build up a compression. For this purpose, the rail-like straight guide 7 is surrounded by guide tubes 11 having the same cross-sectional shape (i.e. having a square internal cross-section) as the rail 7.

In the prior art, the clamp nails 4 are provided with an external thread 9, with the aid of which they can be screwed through the respective end of the arm towards the ilium 5 (arrow 10 in FIG. 1*b*). As a result, the arms 6 clamp against the sliding guide 7 (and the guide tubes 11 are relatively short for this purpose) or said sliding guide will even bend slightly.

Consequently, the position of the pelvic clamp 2 on the body of the patient 1 is secured. However, the relatively short guide tubes 11 also provide a less advantageous straight guidance along the rail 7.

With reference to the arrow 10, it is now easy to understand that careful screwing in with precisely the required force is no easy task and is also time-consuming. Furthermore, it is clear that the forces acting on the clamp nails result, at the free end of the arms 6, in a relatively high moment on the rail 7, which, however, is actually intended because canting was actually intentionally brought about for fixing the arms 6 on the straight guide 7, which canting, however, once again proved to be problematic when subsequently loosening the pelvic clamp 2.

Figure 2:
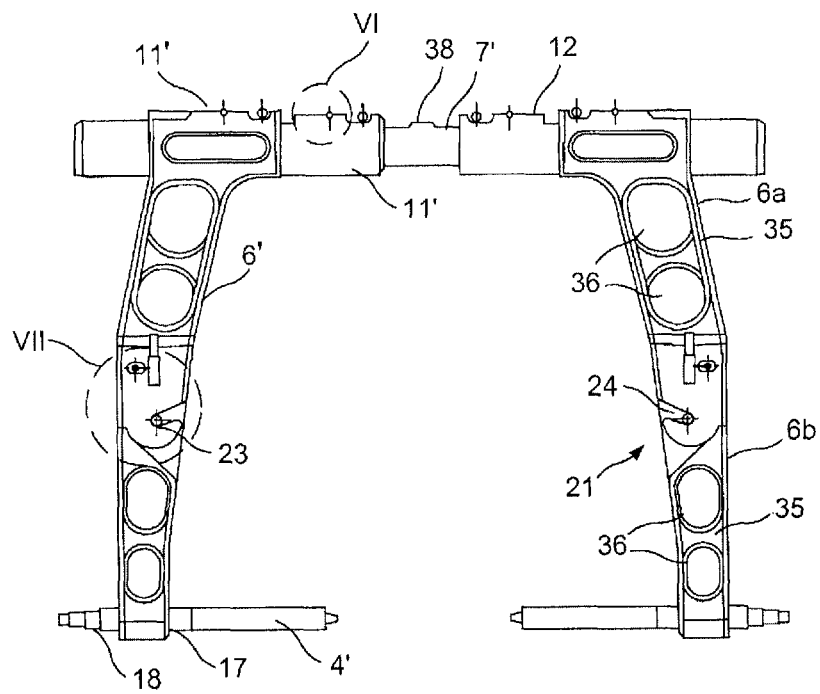
FIGS. 2 and 3 show a side view of a preferred embodiment in the working position (FIG. 2) and in the rest or transport position (FIG. 3)
Figure 3:
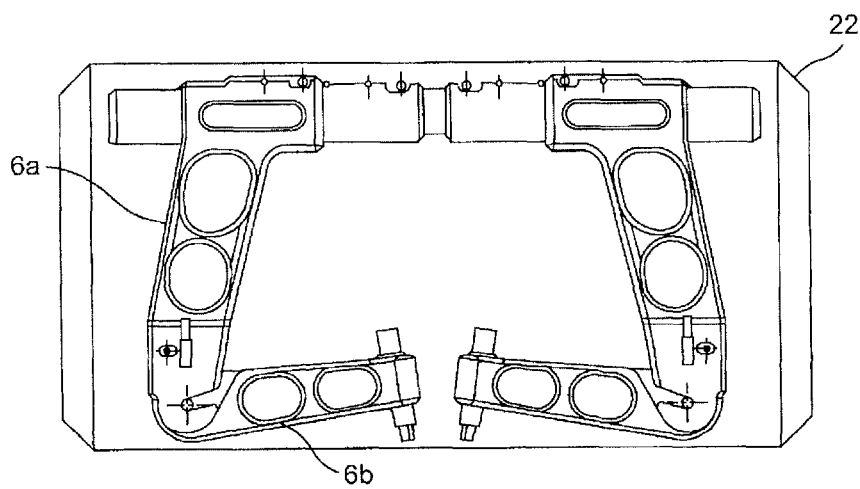

FIGS. 2 and 3 illustrate a solution to these handling problems. Parts having identical functions have the same reference numerals as in FIGS. 1a and 1b, and parts having a similar function have the same reference numerals with an additional character.

In the case of FIG. 2, the parts 4, 6, 7 and 11 therefore appear as parts 4', 6', 7' and 11', 7' corresponding to a guide unit and not a guide rod. However, it is clear that the guide tubes 11' are relatively longer in comparison with those of FIG. 1a (e.g. lengthened by a guide sleeve 11" holding a handle 12) and may account, for example, for up to half of the total length of the arm 6'. Expediently, however, the length is below this value simply to avoid hindering the pushing together of the arm 6', a value of 20% to 30%, e.g. about a quarter of the length of the arms 6', offering both good guidance and being non critical with respect to the pushing together. The arms 6' are therefore pushed together exactly as the arms 6 of FIG. 1a (cf. arrows 8). However, in order then to fix the arms, the locking device which can be released by means of a handle 12 is provided, a preferred embodiment of which is now to be described with reference to FIG. 6.

Figure 6:
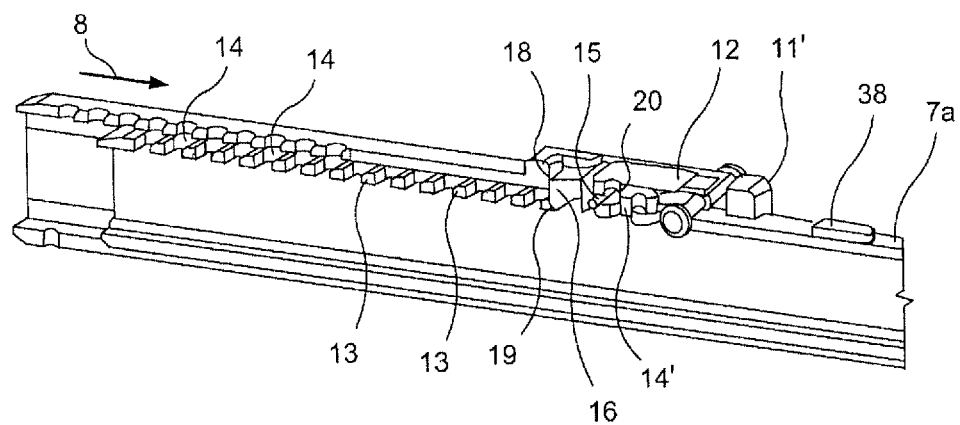
FIG. 6 shows the detail VI of FIG. 2 in a preferred embodiment on a larger scale.

In order to be able to achieve complete locking of the C-clamp after mounting on the patient, the mechanism shown in FIG. 6 was developed. A slide is moved longitudinally in a groove provided, until said slide locks with the handle.

According to FIG. 6, the guide unit 7 has a sort of toothed rack 7a having teeth 13 and indentations 14 located in between. The toothed rack 7a is part of the guide unit from which the indentations 14 are machined out. Of course, it is also possible to choose simpler constructions for the intended function of locking, in fact all that is important here is that a bolt falls into one of the indentations 14. A possibly applicable construction principle will be described later—but for a slightly different purpose—with reference to FIG. 7.

In FIG. 6, only the upper part of the left (based on FIG. 2) guide tube 11' on the toothed rack 7a is shown. This upper part carries a catch pivoting about an axle 15 and formed at its top as handle 12 and having a catch lug 16 playing the role of a projection engaging the indentations 14. By inserting the catch lug 16 into one of the indentations 14, it is therefore possible to lock the associated arm 6' (FIG. 2) in its respective position. All that is necessary is to push the arms 6' together in the direction of the arrows 8 (FIG. 1a) until the desired position is reached, and then to fix them in this position by means of the locking device 14, 16. Since the surgeon does not grip the free end of the arms and moreover there is a greater guide length of the tubes 11', there is scarcely any problem of canting. On the other hand, the arms 6' (or at least one arm, since the other could in fact be fixed to the rail 7) can easily and quickly be pushed towards one another.

It is preferable if the locking device 14, 16 is in the form of a sort of ratchet, as is now to be explained with reference to FIG. 6. Starting from the above explanation that FIG. 6 shows the upper part (guide tube 11') of the arm 6' shown on the left in FIG. 2, the catch lug 16 has an approximately vertical blocking surface 18 which is directed towards this left arm and rests firmly against the respective tooth 13 and thus prevents a backward movement of the guide tube 11' (i.e. to the left, based on FIG. 6). The compressive force acts at the end face on the catch top 18 so that the moveable elements (rails, straight guides) are blocked. In contrast, on the other side, i.e. towards the opposite arm 6' (not shown in FIG. 6), the catch lug 16 has an oblique surface 19 which is directed towards this other arm 6' and, on pushing in the direction of the arrow 8, slides without great resistance over the respective adjacent right tooth and then falls again into the next indentation. This ratchet construction therefore facilitates the pushing together, the respective arm being prevented from moving in the opposite direction (to the left in FIG. 6). Thus, for example, two torsion springs 20 act as restoring springs (one might be enough) on the catch lug 16. The development according to the invention effectively provides automatic locking by virtue of the fact that the catch snaps into each of the indentations, for example by spring force.

A few details may be mentioned here: in principle, a single indentation would in fact be sufficient when the dimensions of the patients were always the same; a toothed rack 7a is therefore not absolutely essential; rather a few indentations 14 can also be distributed along the rail 7. Furthermore, it is clear that the construction could also be the reverse, in that the rack 7a has individual, e.g. pin-like, projections which are engaged by an "indentation", for example in the form of a hook or eye on the catch 12, 16. Although it is preferable to arrange the locking device 13-19 on the top or the upper surface of the rail 7, the invention is by no means limited thereto; rather handles which can be pressed together with two fingers could be provided for one locking device each, for example on both sides of the guide tube 11'. It is furthermore clear that the toothed rack 7a advantageously has a spacer 38 in the middle region (where the catches of the left and right arm may meet).

Returning to FIG. 2, it is clear there, and in comparison to FIG. 3, that the arms 6' are in two parts. The first section 6a is connected at one end to the guide tube 11'. Its other end carries a second section 6b by means of a joint designated in general by 21 and/or a coupling. This arrangement effectively makes it possible to fold together the sections of the respective arm 6' in a transport position (FIG. 3) and thus to bring them to a less cumbersome position in which the pelvic clamp according to the invention can be stored in a compact manner in a transport case 22. It should be mentioned that it is also possible to house the pelvic clamp according to the invention in a so-called tray, i.e. a container having at least one perforated wall which serves for housing in a sterilisation apparatus, a disinfecting gas, in particular dry steam or the like, penetrating through the perforation holes. Trays of this type are disclosed, for example, in WO 99/44717, DE 33 40 963 or U.S. Pat. No. 4,883,321.

Furthermore, the handling of the pelvic clamp according to the invention is facilitated if the weight is reduced. For this purpose, at least the two arm sections 6a, 6b of this preferred embodiment consist of a light metal, such as aluminium (if need be duraluminium or magnesium). It is also advantageous if —as shown— the arm sections are designed in the form of lattice girders which have a strut material 35 only in the regions of the main forces, but openings 36 in between. It is clear that other parts of the pelvic clamp according to the invention may also consist of a light metal, it not being necessary to use the same light metal in each case.

As already evident from FIG. 2, the joint 21 has a joint axle 23 which can be inserted into a receiving slot 24 provided at the end of the section 6a. In this respect, it is therefore a sort of plug-in coupling. However, there is now the problem that the two sections 6a, 6b of the arm 6' have to be rigidly connected to one another in the position of use shown in FIG. 2. The manner in which this is preferably effected is most clearly evident from FIG. 7. There, the joint end of the arm section 6a is shown connected to the joint 21, its axle 23 and the upper end of the arm section 6b.

Figure 7:
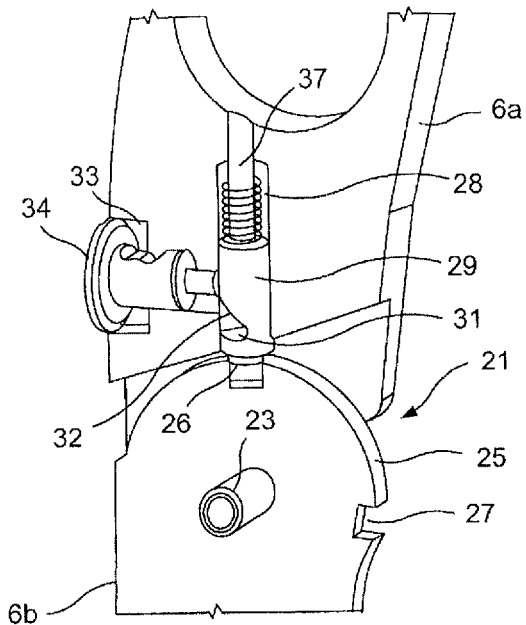
FIG. 7 shows the detail VII of FIG. 2, likewise on a larger scale.

Accordingly, the joint end of the arm section 6b ends in a joint arc 25 which is provided on its circumference with at least one indentation 26 for fixing the position, namely the working position shown in FIG. 2. As shown in FIG. 7, the joint arc 25 is a sort of disc which is formed concentrically with the axle 23. In principle, however, the joint arc actually need correspond only to a part of a circle, in fact it need only be so long that the indentation 26 and if need be a further indentation 27 for fixing the transport position shown in FIG. 3 can be accommodated thereon.

A bolt 29 mounted on the arm section 6a and displaceable in a bore 28 is capable of engaging the indentations 26 or 27 in order to fix the respective relative position of the sections 6a and 6b. However, if desired, the indentations 26 or 27 can of course be replaced by bolts which are mounted there and which cooperate with an indentation provided instead of the bolt 29 on the section 6a. The bolt 29 has a lug-like appendage (not shown) and an indentation 31, by means of which it can be pushed via an actuating handle 34 in the longitudinal direction of the bore 28 in order to disengage from the respective indentation 26 or 27 and move out of the locking position shown in FIG. 7 and thus permit swivelling of the arm section 6b relative to the arm section 6a. As shown for example, the indentation 31 has an oblique surface 32, along which a pusher or pin serving as an actuating handle 34 and displaceable in a stepped bore 33 of the arm section 6a can slide, in order to move the bolt 29 in the bore 28, for example against the pressure of a pressure spring 37 housed above in the vertical bore 28, for pushing the bolt onto the respective indentation 26 or 27. In FIG. 7, the lug-like appendage may be in a retracted disposition within the bolt 29 (in an unlocked state) and may extend into the respective indentation 26 or 27 (in a locked state).

It should be mentioned here that the fixing device described above has a function similar to that of the locking device 13-19 which was described with reference to FIG. 6. It is therefore clear that, for example, the locking device could also be formed in a manner similar to the fixing device 26-33, namely with only one or two indentations and a corresponding releasable bolt.

Figure 4:
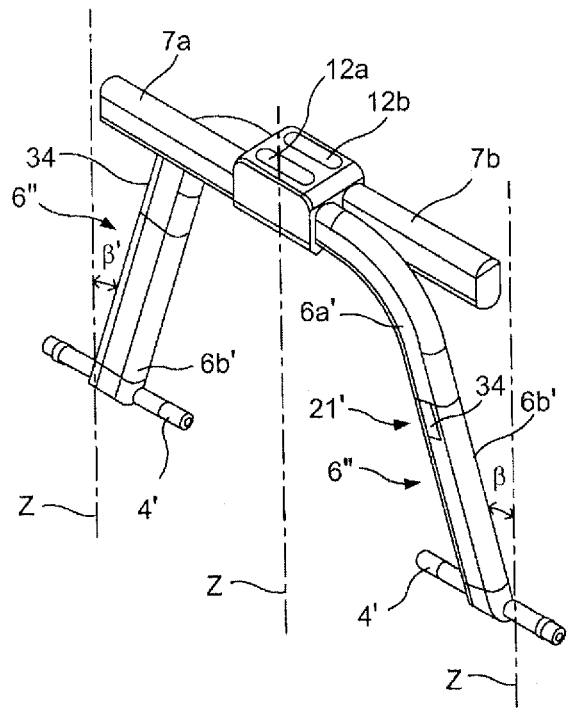
FIGS. 4 and 5 show variants of the straight guide in a perspective view.
Figure 5:
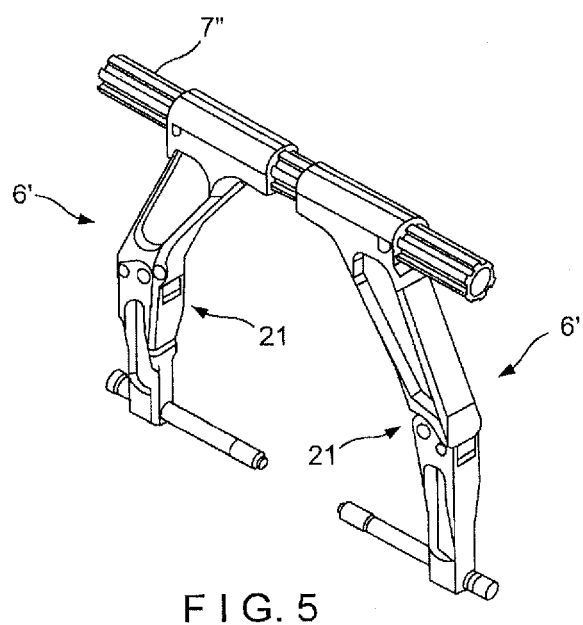

With reference to FIGS. 4 and 5, it is intended to show that, within the scope of the invention, numerous modifications are possible without departing from the protection provided by the patent Claims. Instead of the joint 21 of FIGS. 2 and 6, a simple plug connection is provided in the case of FIG. 4 in a manner such that the lower arm section 6b' can be inserted into the upper arm section 6a' (plug connection 21').

The section 6b' is expediently fixed in this position by means of a fixing device releasable by a push button 34, for example of the type as was described with reference to FIG. 7. For transport the section 6b' can then be withdrawn from the section 6a' after releasing such a fixing device. In comparison with FIG. 2, it immediately becomes clear why the solution according to FIG. 4 is not so preferable, namely because, in the case of FIG. 2, the section 6b remains connected to the section 6a even in the transport position (FIG. 3) whereas, in an embodiment according to FIG. 4, the arm section 6b' constitutes a part which is separated in the transport position and can therefore be lost. In one variant, this disadvantage could be eliminated by a wire- or chain-like securing means to prevent loss.

In contrast, the solution according to FIG. 4 has an advantage in that the straight guide is in the form of two rails 7a, 7b of half length (in comparison to FIG. 2) and can thus be pushed together for size reduction in the transport position for which purpose the locking device in FIG. 4 (not shown) which is provided according to the invention and can be actuated via two handles 12a, 12b here may be helpful. However the result of this is that the planes in which the two arms 6" extend are no longer the same. If it is assumed that the dash-dot lines Z lie in a central plane, it is clear that the right arm 6" is inclined forwards at an angle β to this central plane Z, whereas the left arm 6" assumes an angle β' (in principle of the same magnitude as the angle β but on the other side of the central plane Z). This is preferable for ensuring that, at the lower end (based on FIG. 4) of the arms 6", the two clamp nails 4' lie in the central plane Z and hence opposite one another. However, this means that tolerances in this respect are virtually impossible in this solution.

As shown in FIG. 5, which once again illustrates arms 6' having a joint 21, it is not absolutely essential for the purposes of linear guidance for the rail 7" to have a square cross-section like the rail 7 of FIG. 2 (the locking device for the arms 6" is not shown here). Rather, the rail 7" has, as is evident at the end, a toothed cross-section, but is in general round. If the lever arm provided by the arms 6' and the force acting on the arms 6' are now considered it is clear that such a round rail 7" may be subjected to a stronger torsion than the rail 7' of square cross-section in FIG. 2, and it is for this reason that the development according to FIG. 5 is less preferred.

Numerous modifications are possible within the scope of the invention; for example, it was already mentioned that one of the arms could be firmly connected to the straight guide rail 7'. Furthermore, the locking devices for the two arms need not be identical, although this is of course preferred. It is also clear that FIG. 2 could also be formed without plug connection and without slot 24. Furthermore, although it is preferably if this slot 24 is formed on the respective side facing the other arm 6', because the forces acting on the arm and the joint 21 can then be better absorbed, an arrangement on the side facing away from the respective arm 6' is also entirely possible if the sliding of the axle 23 out of the slot is then prevented by a corresponding blocking device (which, however, then also means additional effort).

List of Reference Numerals

1—Patient
2—Pelvic clamp
3—Kirschner wire
4—Clamp nail
4'—Clamp nail
5—Ilium
6—Arm
6'—Arm
6"—Arm
6a—First arm section
6b—Second arm section
6'a—Upper arm section
6'b—Lower arm section
7—Rail, rail-like straight guide, sliding guide
7'—Rail, rail-like straight guide, sliding guide
7"—Rail
7a—Toothed rack, rail 7b—Rail
8—Arrow
9—External thread
10—Arrow
11—Guide tube
11'—Guide tube
12—Handle
12a—Handle
12b—Handle
13—Teeth (locking device)
14—Indentations (locking device)
14'—Indentations (locking device)
15—Axle (locking device)
16—Catch lug (locking device)
17—Broadened collar (locking device)
18—Catch top, blocking surface (locking device)
19—Oblique surface (locking device)
20—Torsion spring
21—Joint
21'—Plug connection
22—Transport case
23—Joint axle
24—Receiving slot
25—Joint arc
26—Indentation (fixing device)
27—Indentation (fixing device)
28—Bore
29—Bolt (fixing device)
31—Indentation (fixing device)
32—Oblique surface (fixing device)
33—Stepped bore (fixing device)
34—Push button
35—Transport case
36—Openings
37—Pressure spring (fixing device)
38—Spacer
Z—Central plane

The invention claimed is:

1. A pelvic clamp, comprising:
a substantially straight rail-like guide;
first and second arms displaceable relative to one another along the guide, each of the first and second arms including a first end and a second end, the first ends including respective guide tubes configured to couple each of the respective first and second arms to the guide, a length of each of the guide tubes being 20-50% of a length of a respective one of the first and second arms;
first and second substantially tubular carriers disposed at the second ends of each of the first and second arms, each of the first and second carriers adapted to receive a bone contacting tip;
a first locking device including a first locking part disposed on the guide and a second locking part disposed on an inner surface of the first end of the first arm so that when the first arm is in a desired position, the first locking part couples to the second locking part to lock the first arm with respect to the guide; and
a first actuator coupled to the first locking device for releasing the first locking device to free the first arm to move relative to the guide.

2. The pelvic clamp according to claim 1, wherein the first actuator includes a handle.

3. The pelvic clamp according to claim 1, wherein the first locking part includes at least one indentation on the guide and the second locking part includes at least one corresponding projection on the first end of the first arm, the at least one indentation engaging the corresponding projection to lock the first arm relative to the guide.

4. The pelvic clamp according to claim 3, wherein the at least one indentation includes a plurality of indentations and wherein the at least one projection includes a plurality of projections corresponding to the plurality of indentations.

5. The pelvic clamp according to claim 1, wherein the first locking device includes a catch formed as a ratchet including an oblique surface and a restoring spring, the catch being disengagable by a sheer force acting on the first arm along the guide toward the second arm against a biasing force of the restoring spring, the catch being prevented from moving toward the first arm by a blocking surface until the locking device is released by the first actuator.

6. The pelvic clamp according to claim 1, further comprising: a second locking device including a third locking part disposed on the guide and a fourth locking part disposed on the first end of the second arm so that when the second arm is in a desired position, the third locking part couples to the fourth locking part to lock the second arm with respect to the guide, the second locking device being releasable to free the second arm to move relative to the guide.

7. The pelvic clamp according to claim 1, wherein at least one of the first and second arms is foldable about a first joint, the first joint being fixable in a plurality of predetermined positions via a first plug connection.

8. The pelvic clamp according to claim 7, wherein the other of the first and second arms is foldable about a second joint, the second joint being fixable in a plurality of predetermined positions via a second plug connection.

9. The pelvic clamp according to claim 7, wherein the first joint includes a joint arc and an indentation into which a projection is insertable defining a first one of the predetermined positions on one of the arc and a section of the one of the first and second arms opposite the arc.

10. The pelvic clamp according to claim 9, wherein the projection is a bolt.

11. The pelvic clamp according to claim 1, wherein at least one part of the pelvic clamp consists of a light metal.

12. The pelvic clamp according to claim 1, wherein at least one part of the pelvic clamp consists of one of aluminum and an aluminum alloy.

13. The pelvic clamp according to claim 1, wherein the guide includes a rail having a substantially tetragonal cross-section with four outer surfaces, and wherein the locking device is at least partially mounted on one of the outer surfaces with which the actuator cooperates to release the locking device.

14. The pelvic clamp according to claim 1, wherein the guide has at least one rail having a substantially square cross-section.

15. The pelvic clamp according to claim 1, wherein the first carrier is fixed on the second end of the first arm so that it is prevented from movement along an axis of the carrier via a fixing arrangement.

16. The pelvic clamp according to claim 1, wherein the second locking part includes a substantially vertical surface to prevent a backward movement of the guide and an oblique surface so that the first arm is movable in only a first direction.

17. The pelvic clamp according to claim 16, wherein when the first locking device is released, the first arm is freed to move relative to the guide in a second direction opposite the first direction.

18. The pelvic clamp according to claim 1, wherein the length of each of the guide tubes is 20-30% of a length of a respective one of the first and second arms.

\* \* \* \* \*